United States Patent
Hansen et al.

(10) Patent No.: US 12,055,506 B2
(45) Date of Patent: Aug. 6, 2024

(54) STANDARDIZING THE OUTPUT OF AN ELECTRICAL PROPERTY SENSOR

(71) Applicant: Foss Analytical A/S, Hilleroed (DK)

(72) Inventors: Per Waaben Hansen, Hilleroed (DK); Mads Lykke Andersen, Hilleroed (DK)

(73) Assignee: FOSS Analytical A/S, Hilleroed (DK)

( * ) Notice: Subject to any disclaimer, the term of this patent is extended or adjusted under 35 U.S.C. 154(b) by 240 days.

(21) Appl. No.: 17/632,043

(22) PCT Filed: May 28, 2020

(86) PCT No.: PCT/IB2020/055064
§ 371 (c)(1),
(2) Date: Feb. 1, 2022

(87) PCT Pub. No.: WO2021/038315
PCT Pub. Date: Mar. 4, 2021

(65) Prior Publication Data
US 2022/0276189 A1  Sep. 1, 2022

(30) Foreign Application Priority Data
Aug. 29, 2019 (DK) .............................. PA201901018

(51) Int. Cl.
*G01N 27/06* (2006.01)
*G01N 21/3577* (2014.01)
*G01N 33/04* (2006.01)

(52) U.S. Cl.
CPC ......... *G01N 27/06* (2013.01); *G01N 21/3577* (2013.01); *G01N 33/04* (2013.01)

(58) Field of Classification Search
CPC .... G01N 21/3577; G01N 27/06; G01N 33/04; G01N 21/31
(Continued)

(56) References Cited

U.S. PATENT DOCUMENTS

| | | | |
|---|---|---|---|
| 2008/0290279 A1 | 11/2008 | Juhl | |
| 2016/0091432 A1* | 3/2016 | Clark | G06Q 30/0282 422/429 |
| 2019/0242816 A1* | 8/2019 | Conner | G01N 27/06 |

FOREIGN PATENT DOCUMENTS

| | | |
|---|---|---|
| EP | 1266668 A1 | 12/2002 |
| JP | H0755744 A | 3/1995 |

(Continued)

OTHER PUBLICATIONS

International Search Report and Written Opinion for International Application No. PCT/IB2020/055064 dated Aug. 11, 2020.

(Continued)

*Primary Examiner* — Eman A Alkafawi
*Assistant Examiner* — Courtney G McDonnough
(74) *Attorney, Agent, or Firm* — Harness, Dickey & Pierce, P.L.C.

(57) ABSTRACT

A method of standardizing an output of an electrical property sensor includes calculating a reference magnitude ($Cond_r$) of an electrical property of an electrically conductive liquid, based on obtaining, by a spectrometer, spectral data resulting from an interaction of light with the electrically conductive liquid, and applying, in a data processor, a mathematical model to the spectral data to calculate the reference magnitude ($Cond_r$) of the electrical property, wherein the mathematical model links the spectral data to magnitudes of the electrical property; comparing, in the data processor, a measured magnitude ($Cond_m$) of the electrical property of the electrically conductive liquid with a reference magnitude ($Cond_r$) of the electrical property, wherein the measured magnitude ($Cond_m$) of the electrical property is obtained with the electrical property sensor; determining, in the data processor, a standardization factor (F) dependent (Continued)

on a ratio of the reference magnitude ($Cond_r$) and the measured magnitude ($Cond_m$).

9 Claims, 6 Drawing Sheets

(58) Field of Classification Search
USPC .......................................................... 324/442
See application file for complete search history.

(56) References Cited

FOREIGN PATENT DOCUMENTS

| WO | WO-2000039578 A2 | 7/2000 |
|---|---|---|
| WO | WO-2014205230 A1 | 12/2014 |
| WO | WO-2018045349 A1 | 3/2018 |

OTHER PUBLICATIONS

DKSR for Danish Application No. PA201801018 dated Dec. 2, 2019.

Cuadros-Rodriguez et al., "Calibration in Chemical Measurement Processes", Trends in Analytical Chemistry, vol. 20, No. 11, 2001.

* cited by examiner

STANDARDIZING THE OUTPUT OF AN ELECTRICAL PROPERTY SENSOR

CROSS-REFERENCE TO RELATED APPLICATIONS

This application is a National Stage of PCT/IB2020/055064, filed on May 28, 2020, which claims priority to Danish Patent Application PA201901018, filed on Aug. 29, 2019 in the Danish Patent and Trademark Office, the entire contents of each of which are incorporated herein in their entirety.

BACKGROUND

The present invention relates to standardizing the output of an electrical property sensor and in particular to the output of an electrical conductivity sensor employed in an analyser also including an optical spectrometer.

It is known to provide analysers which comprise not only an electrical property sensor but also a spectrometer. U.S. Pat. No. 5,739,034, for example, discloses an analyser employing both an electrical conductivity sensor and a spectrometer in order determine extraneous water in milk. Changes in water content of the milk results in changes in the milk's conductivity, which changes are monitored using the conductivity sensor. WO 2000039578, for example, discloses an analyser which also comprises an electrical conductivity sensor and a spectrometer which are configured to be used together to estimate a cell count in milk. Mastitis infection is associated with an increased content of salts in the milk, which causes an increase in the electrical conductivity of the milk.

It is often desirable to standardise the output of the conductivity sensor, at least in order to facilitate the comparison of sensor outputs of different sensors of the same type or the outputs of the same sensor at different times and also in order to allow for the use of the same mathematical models on data from different sensors.

Such standardisation is presently typically performed by introducing a standardisation material, such as a liquid, into the analyser and measuring the electrical conductivity of this material using its electrical conductivity sensor. The measured magnitude of the electrical conductivity is then compared in a data processor with a reference magnitude expected to be produced by the material and stored for access by the data processor. A standardization factor is then determined that is dependent on a ratio of the reference magnitude and the measured magnitude. This may be subsequently applied to a measured magnitude of the conductivity of an unknown sample material obtained with the conductivity sensor in order to obtain a standardised output from the electrical conductivity sensor.

A problem with this known standardisation method is that the amount of the components in the standardisation material (liquid) which give rise to its electrical property or properties to be measured must be carefully controlled in order to ensure that different batches of the standardisation material exhibit a same and a known reference magnitude of its electrical property or properties to be measured by the sensor, which in the above cases is its electrical conductivity.

SUMMARY

According to the present invention there is provided a method for standardizing an output of an electrical property sensor comprising the steps of: comparing in a data processor a measured magnitude of the electrical property of an electrically conductive liquid obtained with the electrical property sensor with a reference magnitude; and determining in the data processor a standardization factor dependent on a ratio of the reference magnitude and the measured magnitude; wherein there is provided a step of calculating the reference magnitude comprising: obtaining by a spectrometer spectral data resulting from an interaction of light with the electrically conductive liquid, the light comprising wavelength bands which contain at least a portion of one or more ultraviolet, visible and infrared regions; and applying in the data processor a mathematical model to the spectral data to calculate the reference magnitude, which mathematical model links spectral data to magnitude of the electrical property.

This has an advantage that since the reference magnitude is calculated for the electrically conductive liquid from spectral data obtained from the actual liquid which is being employed in the electrical property standardisation measurements then the exact concentration of components comprising the liquid need neither be known nor accurately reproduced between different batches.

The so determined standardisation factor is subsequently applied in the data processor to a measured magnitude of the electrical property of a sample liquid obtained with the electrical property sensor in order to obtain a standardised measure of the electrical property of the sample liquid.

In some embodiments the electrically conductive liquid is a "consumable liquid", for example a cleaning liquid or a zero setting liquid (used in a known fashion to establish a baseline spectrum for subsequently collected sample spectra), which is a liquid that is used in the analyser but which is not a sample to be analysed. This has an advantage that no extra liquids need be introduced into the analyser and the method may be performed using measurements obtained during its normal operation, for example during a reference or 'zero setting' cycle of the analyser.

The mathematical model may be obtained by chemometric analysis or machine learning method such as an analysis employing Partial Least Squares (PLS) regression, or other multivariate calibration techniques such as Principle Component Analysis (PCA), Multiple Linear Regression (MLR) or Artificial Neural Networks (ANN), applied to spectral data obtained from a set of reference samples having known magnitudes of the electrical property (or properties) to be measured, the values of which are selected to span a range of values expected for the electrically conductive liquid sample to be measured in the generation of the standardisation factor.

BRIEF DESCRIPTION OF THE DRAWINGS

These and other advantages associated with the present invention will become apparent from a consideration of the following description of aspects of non-limiting exemplary embodiments of the present invention which is made with reference to the accompanying figures, of which.

DETAILED DESCRIPTION

Figure 1:
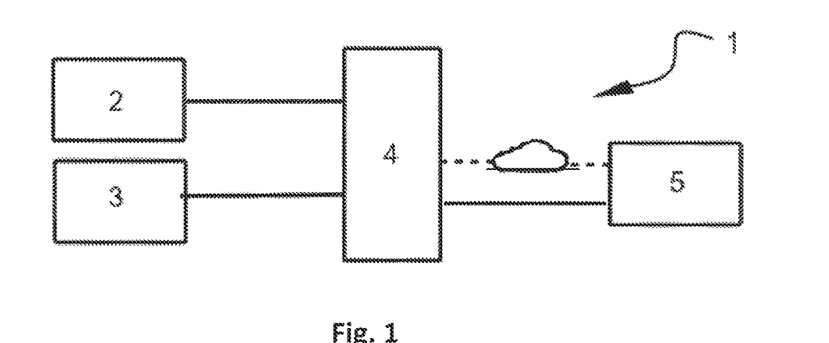
FIG. 1 illustrates a schematic representation of an exemplary embodiment of an analyser according to the present invention.

FIG. 1 schematically illustrates an exemplary embodiment of an analyser 1 according to the invention. A spectrometer 2 is provided which may be of any known type which is able to determine the light attenuation by a liquid sample in at least one waveband in a wavelength region of interest. This wavelength region of interest may comprise wavelength bands which contain the whole or a portion of one or more ultraviolet, visible and infrared wavelength regions. and shall also hereinafter be referred to as 'light'. Fourier Transform (FT) interferometer based instruments are highly suited for this use as the spectrometer 2 since the whole or relevant portions of the wavelength regions of interest for the sample may be obtained in one process. When determining the light attenuation in a sample, light from a light source may be transmitted through the sample and its absorption spectral data collected by the FT interferometer instrument. Of course the FT interferometer, or indeed any other spectrometer, may be configured to operate in reflection or transflection or total internal reflection modes as is known in the art. In the type of which operates in transmission mode, the liquid sample is typically contained in a sample holder, such as a cuvette, which is sufficiently thin so as to permit the passage of the light without total attenuation, but where it is still possible to introduce and remove the sample. The cuvette should be made of a material which is transparent to the wavelengths of light being employed and may be, when infrared light is used, particularly mid-infrared light, made of material such as diamond or $CaF_2$.

Figure 2A:
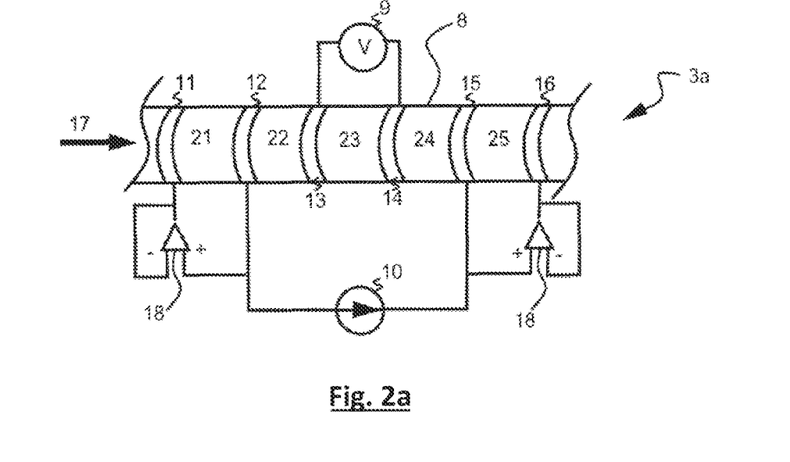
FIG. 2a illustrate schematic representations of two exemplary and 2b embodiments of an electrical property sensor for use in the analyser of FIG. 1.
Figure 2B:
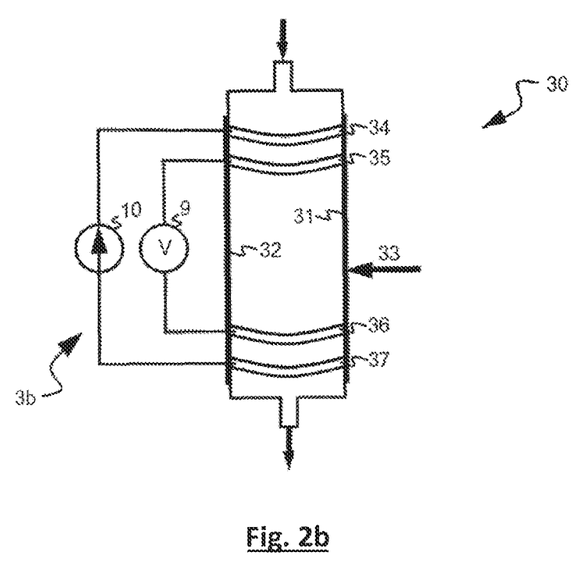

An electrical property sensor 3 for determining the electrical property of the sample may also be of any type able to determine the desired electrical property of a liquid sample. Examples of electrical conductivity type measuring means 3a and 3b are shown in FIG. 2a and FIG. 2b respectively as alternative illustrative exemplary embodiments of the electrical property sensor 3 of this type. Inductive and two-electrode cell type conductivity sensors are examples of other types of conductivity sensor known in the art and which may be employed in the present invention.

The determined light attenuation values for the individual wavebands and the value for the electrical property of the sample are transmitted to data processor 4. These values are stored in storing means 5, which also typically stores computer code executable by the data processor 4 which then causes the data processor 4 to execute the method of the present invention.

Although not required, aspects of the invention may be described in the general context of computer-executable instructions or computer code, such as routines executed by a general-purpose data processor (e.g., a server computer or a personal computer). Those skilled in the relevant art will appreciate that the invention can be practiced with other communications, data processor, or computer system configurations, including: wireless devices, Internet appliances, hand-held devices (including personal digital assistants (PDAs)), wearable computers, all manner of cellular or mobile phones, multi-processor systems, microprocessor-based or programmable consumer electronics, network PCs, mini-computers, mainframe computers, and the like. Indeed, the term "data processor" is used herein to refer to any of the above devices and systems, alone or in combination.

While aspects of the invention, such as certain functions, are described as being performed exclusively on a single data processor or storing means, the invention can also be practiced in distributed environments where functions or modules are shared among disparate processing devices. The disparate processing devices are linked through a communications network, such as a Local Area Network (LAN), Wide Area Network (WAN), or the Internet. In a distributed computing environment, program modules may be located in both local and remote memory storage devices.

Aspects of the invention may be stored or distributed on tangible computer-readable media, including magnetically or optically readable computer discs, hard-wired or pre-programmed chips (e.g., EEPROM semiconductor chips), nanotechnology memory, biological memory, or other data storage media. Alternatively, computer implemented instructions, data structures, screen displays, and other data related to the invention may be distributed over the Internet or over other networks (including wireless networks), on a propagated signal on a propagation medium (e.g., an electromagnetic wave(s), a sound wave, etc.) over a period of time. In some implementations, the data may be provided on any analogue or digital network (packet switched, circuit switched, or other scheme). The term "storing means" is used herein to refer to any of the above devices, media and systems.

In some instances, the interconnection between modules comprising the analyser 1 is the internet, allowing the modules (with, for example, WiFi capability) to access web content offered through various web servers. The network may be any type of cellular, IP-based or converged telecommunications network, including but not limited to Global System for Mobile Communications (GSM), Time Division Multiple Access (TDMA), Code Division Multiple Access (CDMA), Orthogonal Frequency Division Multiple Access (OFDM), General Packet Radio Service (GPRS), Enhanced Data GSM Environment (EDGE), Advanced Mobile Phone System (AMPS), Worldwide Interoperability for Microwave Access (WiMAX), Universal Mobile Telecommunications System (UMTS), Evolution-Data Optimized (EVDO), Long Term Evolution (LTE), Ultra Mobile Broadband (UMB), Voice over Internet Protocol (VoIP), Unlicensed Mobile Access (UMA), etc.

The modules in the systems of the analyser 1 can be understood to be integrated in some instances and in particular embodiments, only particular modules may be interconnected.

FIG. 2a and FIG. 2b illustrate two non-limiting exemplary embodiments of the electrical property sensor 3 of the analyser 1 of the invention, both configured to measure electrical conductivity as the electrical property. It will be appreciated that other known types of electrical conductivity sensor, such as two-electrode or inductive sensors, may be substituted without departing from the invention as claimed.

In the embodiment of this sensor 3a illustrated in FIG. 2a, the liquid sample is contained within a liquid conduit section 8 through which the liquid sample can flow. In this embodiment 6 electrodes 11, 12, 13, 14, 15, and 16 are used; these electrodes are spatially separated in the direction of flow of the liquid sample (see arrow 17).

The electrodes 11-16, made of e.g. stainless steel, which are in direct electrical contact with the sample in the conduit 8, are shaped as circular electrodes, having thicknesses of e.g. 1, 1, 0.1, 0.1, 1, and 1 mm, respectively, which together with a number of electrically non-conducting separation means 21-25, e.g. made of plastics or ceramics (such as aluminium oxide) and having thicknesses of e.g. 1, 3, 3, 3, and 1 mm, respectively, constitute the conduit 8. The electrodes 11-16 and the separating means 21-25 preferably have the same inner diameter, such as 1.5 mm, so as to obtain a smooth inner surface of the conduit 8 and thus to reduce the possibility of sedimentation therein. A smooth conduit 8 also has the advantage that it results is a homogeneous electrical field in the sample. To ensure that the conduit 8 does not leak the sample, the separation means 21-25 and the electrodes 11-16 may be assembled using O-rings as known per se.

The two middle electrodes 13, 14 are connected to a voltage-meter 9. The two adjacent electrodes 12, 15 are connected to a current supply 10, whereby a current is transmitted through the part of the sample situated in the conduit 8 between the electrodes 12 and 15. The voltage across the electrodes 13 and 14 relative to the transmitted current will thereby give an indication of the electrical conductivity of the sample in the conduit 8.

In this way, the electrical conductivity of the sample may be determined from the voltage difference between the electrodes 13 and 14, the size of the current fed by the electrodes 12 and 15, and a geometry factor, which may be determined on the basis of a suitable calibration of the electrical conductivity measuring means.

When using four electrodes in this configuration, the sensor 3a is less dependent on fouling of the electrodes and on polarization effects. Furthermore, if alternating current is fed to the electrodes 12, 15, electrolysis and polarization at the surfaces of these electrodes is eliminated.

Two additional electrodes 11, 16 are positioned adjacent to the current-feeding electrodes 12, 15. These additional electrodes are fed with the same potential as the adjacent electrodes 12, 15, respectively. In this way, no current is leaked from the sensor 3a, falsifying the conductivity determination.

In the present embodiment, the potential fed to the additional electrodes 11, 16 is generated by operational amplifiers 18 which are connected as "voltage-followers" following the potential of each of the electrodes 12 or 15, In this way, the potential of the electrodes 12 and 15 are not altered to any significant degree by the additional electrodes 11 and 16 following the potential of electrodes. In an analyser 1 which employs this embodiment 3a of electrical property sensor 3 the spectrometer 2 is connected in liquid communication either before or after the liquid conduit section 8 in the direction of liquid flow 17.

In the embodiment of this sensor 3b illustrated in FIG. 2b, the liquid sample is held by a cuvette 30, at least a portion of which (here opposing sides 31 and 32) comprises a material transparent to light to be measured by the spectrometer 2. In embodiments where the light to be measured is mid-infrared light then this material may be calcium flouride, $CaF_2$. In the present embodiment substantially the entire cuvette 30 comprises this material. In use, light (see arrow 33) enters the cuvette through wall 31, is transmitted through liquid sample inside the cuvette 30 where wavelength portions are differently absorbed, and exits the cuvette 30 through the wall 32 after which it is detected in the spectrometer 2 to generate wavelength dependent spectral absorption data to be stored in storing means 5 accessible by the data processor 4 for subsequent data analysis.

The conductivity sensor 3b is constructed essentially as described with regard to the sensor 3a of FIG. 2a and here comprises 4 electrodes 34-37 attached to or forming a part of the cuvette 30 to make electrical contact with sample liquid inside the cuvette 30. These electrodes 34-37 may be formed as vapour deposited gold layers on the inside of the cuvette walls 31, 32 and are separated by electrically insulating material of the cuvette 30, typically the wall material. As with the conductivity sensor 3a described above in connection with FIG. 2a, the two middle electrodes 35, 36 are connected to a voltage-meter 9. The two adjacent electrodes 34, 37 are connected to a current supply 10, whereby a current is transmitted through the part of the sample situated in the cuvette 30 between the electrodes 12 and 15. The voltage across the electrodes 13 and 14 will thereby give an indication of the electrical conductivity of the sample in the cuvette 30. With this arrangement electrical conductivity may be measured using the conductivity sensor 3b essentially simultaneously with the measurement of the light attenuation by the spectrometer 2.

In some embodiments, the sensor 3 for measuring the electrical conductivity of the sample is thermostated to within 0.1° C. of a given constant temperature, such as 42° C. when unknown milk samples are to be analysed, as the electrical conductivity of liquid samples is often temperature dependent. In some embodiments the actual temperature of the sample is measured to a required degree of accuracy and the electrical conductivity measurement mathematically corrected to a reference temperature based on this measured temperature.

As also the light absorption of liquid samples may be temperature dependent, then the cuvette in which the sample interacts with the selected light may also be thermostated. Thus, it may be advantageous to position the means 2 and 3 adjacent to each other so (or usefully, even integral with one another as the sensor 3b described above) as to reduce the number of places in the system, wherein strict thermostating is required.

Figure 3:
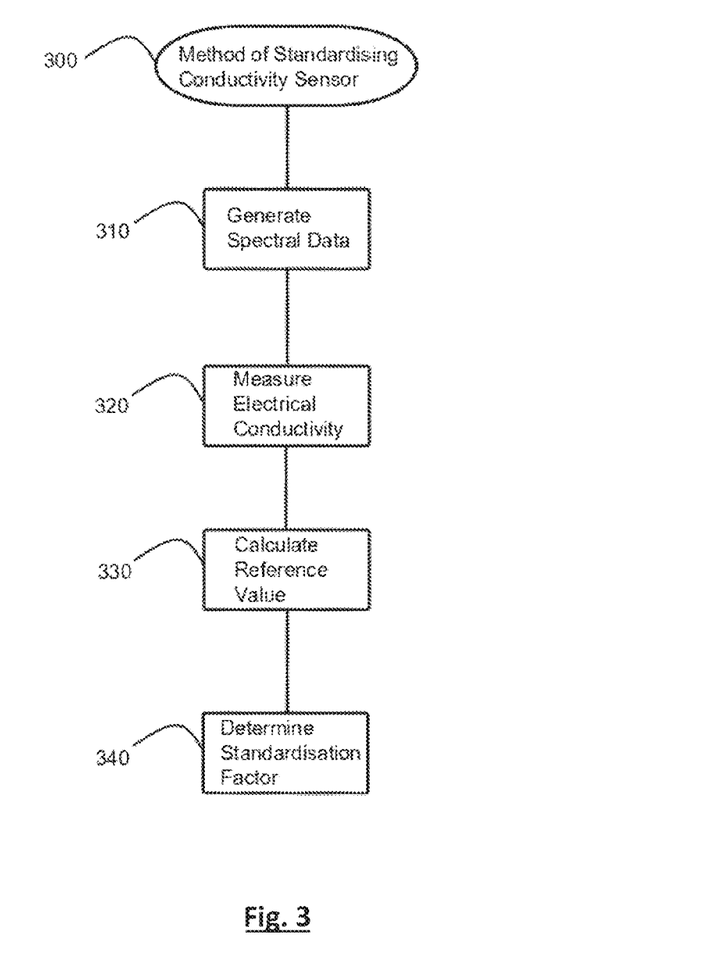
FIG. 3 is a flow diagram illustrating an implementation of the inventive method for standardizing an output of an electrical property sensor.

An exemplary implementation of the method 300 for standardizing an output of an electrical property sensor 3, here an electrical conductivity sensor, is described with reference to FIG. 3.

According to this example, at a step 310, wavelength dependent optical attenuation data for an electrically conductive liquid is obtained by the spectrometer 2 of analyser 1, from which spectral data is generated. The spectrometer 2 may be of any known type such as a one that operates by measuring optical radiation transmitted through or reflected from or radiation having undergone total internal reflection (so called attenuated total internal reflection "ATR" measurements). At this step 310 a liquid, for example a cleaning liquid, a zero liquid or other consumable liquid, having a known relationship between its electrical conductivity and its optical attenuation data, is passed into a measurement cuvette 30 of the FT interferometer based spectrometer 2 and the optical attenuation data, here absorption data, for this liquid is collected and stored in the storage means 5.

At a step 320, the electrical conductivity, $Cond_m$, of this cleaning liquid is measured by using an electrical conductivity sensor 3 such as the sensor 3a illustrated in FIG. 2b which is located in operable connection with a flow conduit in fluid connection with either an inlet or an outlet to the measurement cuvette 30 and through which the cleaning liquid is intended to flow or by using a sensor 3 such as the electrical conductivity sensor 3b illustrated in FIG. 2b which is formed integral with the measurement cuvette 30. The value of the measured electrical conductivity is stored on the storage means 5.

At a step 330 the reference value for the conductivity of this cleaning liquid, $Cond_r$, is calculated by the data processor 4. Coding to implement a mathematical model which links spectral data with conductivity is stored in the storage means 5 and is accessible to and run on the data processor 4. At this step 330 the data processor 4 accesses both the coding for the mathematical model and the spectral data obtained at step 310. The data processor 4 then operates to apply the mathematical model to the spectral data to calculate the reference magnitude of the electrical conductivity, $Cond_r$, of the cleaning liquid which is then stored in the storing means 5.

At a step 340 the data processor 4 retrieves both the measured value for the electrical conductivity ($Cond_m$ obtained at step 320) and the calculated reference value of the conductivity ($Cond_r$ obtained at step 330) from the storing means 5 and generates a standardisation factor, F, dependent on a ratio of the predicted magnitude and the measured magnitude. In certain embodiments this standardisation factor F is determined in the data processor 4 according to the relationship $$F = Cond_r / Cond_m \quad (1)$$

It is known that conductivity is dependent on temperature, T, and in embodiments where there may be poor or no temperature control the standardisation factor F may be improved by correcting the measured value of conductivity $Cond_m$ by a function dependent on temperature f(T). This function f(T) can be determined empirically from measurements at a standard temperature $T_s$ (say 25° C.) on samples having known conductivity and may be expressed as:

$$1/[a(T-T_s)^2 + b(T-T_s) + c] \quad (2)$$

where the coefficients a, b and c are be determined empirically.

The standardisation factor F is stored in the storing means 5 for subsequent use by the data processor 4 to generate a standardised conductivity measurement of sample liquids being analysed by the analyser 1. To this end, the data processor 4 operates to retrieve this standardisation factor F from the storing means 5 and to generate a standardised conductivity measurement $Cond_{std}$ as $$Cond_{std} = F * Cond_{m,s} \quad (3)$$

where $Cond_{m,s}$ is the conductivity of the sample liquid measured by the conductivity sensor 3 (which may or may not be corrected for temperature variations as described generally above with reference to equation (2)).

Figure 4:
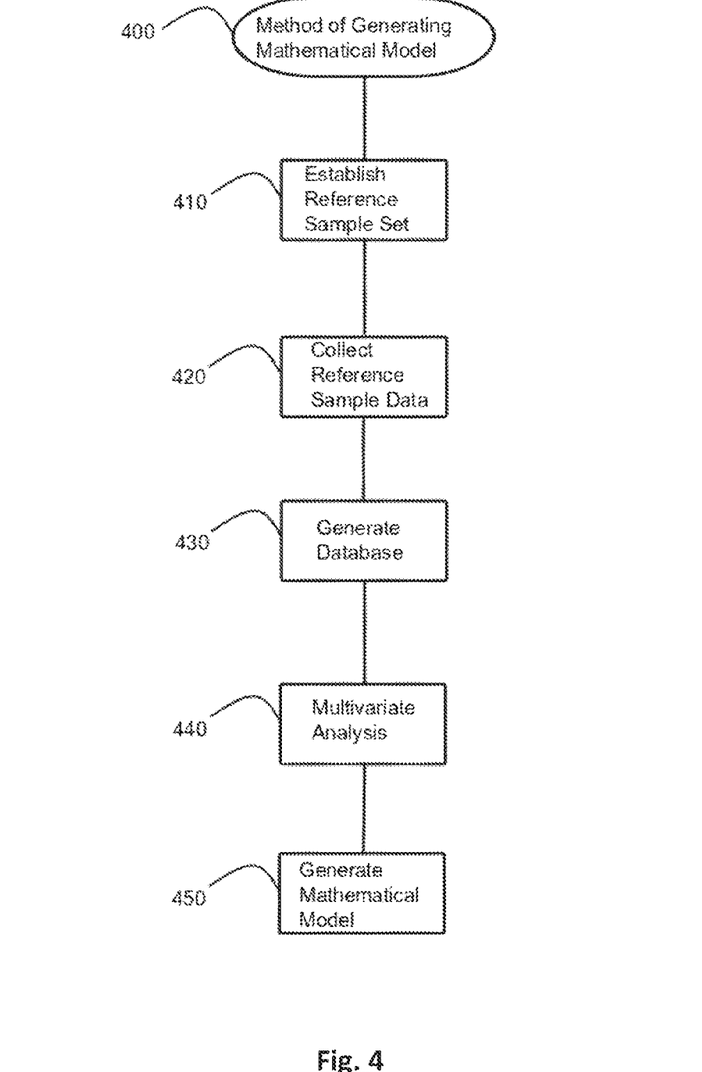
FIG. 4 is a flow diagram illustrating a method of generating a mathematical model for use in the inventive method.

An exemplary embodiment of a method 400 for generating the mathematical model useable in the method 300 for standardizing is described with reference to FIG. 4.

At a step 410 a reference sample set is established consisting of a plurality, here 30, reference liquid samples. The reference liquid samples are generally all liquid samples having the same constituents as the electrically conductive liquid employed in the method 300. In the present embodiment the electrically conductive liquid is a cleaning liquid employed to clean the cuvette 30 and flow conduits of the analyzer 1. The main constituents of both the reference sample liquid and the electrically conductive liquid are therefore, by way of example only, Genapol T 250p, pentasodium triphosphate, SDS, trisodium pyrophosphate, and sodium carbonate. Other constituents may be present but they do not contribute measurably to either the electrical conductivity or the optical properties of the liquids. Generally, each reference liquid sample comprises the same main constituents but each has a different concentration combination of these main constituents. The range of constituent combinations is selected to span the expected variation in constituent combinations of the electrically conductive sample.

At a step 420 spectral data is collected for each liquid sample of the reference sample set, using an apparatus of the same type employed to obtain the absorption data for the electrically conductive liquid at step 310 above, and stored in a storage means.

At a step 430 a database is generated wherein each record includes spectral data for each specific reference liquid sample and a corresponding value for the electrical conductivity of that sample measured using the conductivity sensor 3.

At a step 440 the contents of the database is subjected in the data processor to a multivariate statistical analysis. In the present example this comprises dividing the records of the database into two sets, for example a first and largest set consisting of say 80% of the total number of records and a second set consisting of the remainder of the records of the database to be used for cross-validation, and subjecting the sets to a PLS, here a 10 factor PLS, regression analysis cross validated using three cross validation segments.

At a step 450, a mathematical model is generated in the data processor using the results of the statistical analysis performed at step 440, which model links spectral data to magnitude conductivity. This mathematical model is stored in the storage means of the analyser 1 or is otherwise made available to the data processor for use in calculating the reference magnitude of the conductivity of the electrically conductive liquid from spectral data obtained from that liquid.

Figure 5:
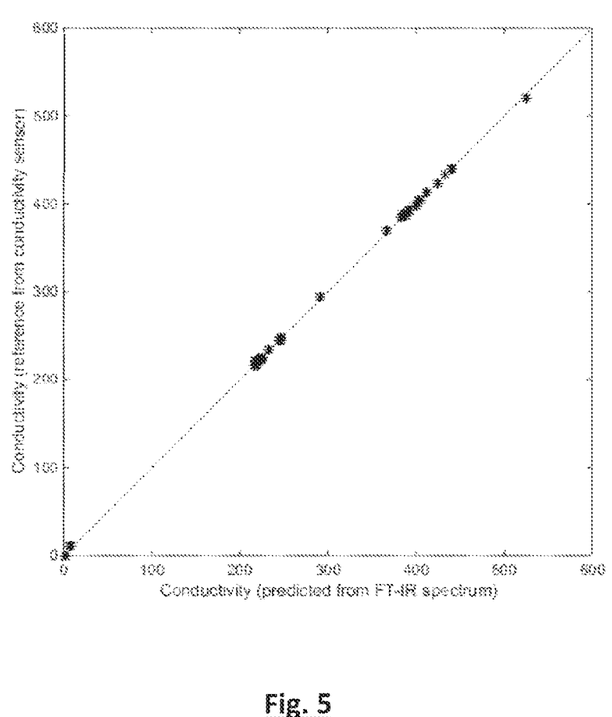
FIG. 5 is a graphical representation of the results of the mathematical model generated according to the method of FIG. 4.

The results obtained using such a model is illustrated graphically in FIG. 5 which shows a plot of measured conductivity for a sample against calculated conductivity obtained from spectral data from that sample using the model. These are summarised in Table 1 below:

| | |
|---|---|
| Conductivity of normal cleaning liquid | 369 (arbitrary units) |
| Number of samples | 30 |
| Number of PLS factors | 10 |
| Prediction error (RMSEP) | 2.0 (0.54% relative) |
| Repeatability ($s_r$) | 0.8 (0.22% relative) |

Since the conductivity can be predicted with a relative error of approx. 0.5% this is also expected to be the error of the standardization of the conductivity sensor 3. This level is considered to be sufficient to ensure a reliable standardization and hence a satisfactory transferability of prediction models using conductivity as one of their inputs, e.g. extraneous water in milk according to the disclosure made in U.S. Pat. No. 5,739,034 referred to above.

The invention claimed is:

1. A method of standardizing an output of an electrical property sensor, the method comprising:
    calculating a reference magnitude ($Cond_r$) of an electrical property of an electrically conductive liquid, based on obtaining, by a spectrometer, spectral data resulting from an interaction of light comprising wavelength bands which contain at least a portion of one or more ultraviolet, visible and infrared regions with the electrically conductive liquid, and
    applying, in a data processor, a mathematical model to the spectral data to calculate the reference magnitude ($Cond_r$) of the electrical property, wherein the mathematical model links the spectral data to magnitudes of the electrical property;
    comparing, in the data processor, a measured magnitude ($Cond_m$) of the electrical property of the electrically conductive liquid with the reference magnitude ($Cond_r$)

of the electrical property, wherein the measured magnitude ($Cond_m$) of the electrical property is obtained with the electrical property sensor;

determining, in the data processor, a standardization factor (F) dependent on a ratio of the reference magnitude ($Cond_r$) of the electrical property and the measured magnitude ($Cond_m$) of the electrical property; and applying, in the data processor, the standardization factor (F) to subsequent measured magnitudes ($Cond_{ms}$) of the electrical property of an electrically conductive sample liquid that are obtained with the electrical property sensor to generate a standardized electrical property measurement ($Cond_{sta}$) of the electrical property of the electrically conductive sample liquid.

2. The method of claim 1, further comprising:

operating the electrical property sensor to generate the measured magnitude of the electrical property for receipt by the data processor, prior to performing the comparing of the measured magnitude ($Cond_m$) of the electrical property with the reference magnitude ($Cond_r$) of the electrical property.

3. The method of claim 1, wherein the mathematical model is generated using chemometric analysis of spectral data from a plurality of reference liquid samples, the plurality of reference liquid samples include constituents that are same constituents as constituents of the electrically conductive liquid, and the plurality of reference liquid samples have different, respective known concentration combinations of the constituents, such that the plurality of reference liquid samples have a range of concentration combinations of the constituents that encompass an expected range of concentrations of the constituents of the electrically conductive liquid.

4. The method of claim 1, wherein the electrical property is conductivity.

5. The method of claim 1, wherein the electrically conductive liquid is a liquid employed to clean an analyser, the analyser including the spectrometer and the electrical property sensor.

6. The method of claim 4, wherein the measured magnitude ($Cond_m$) of the conductivity of the electrically conductive liquid and the subsequent measured magnitudes ($Cond_{ms}$) of the conductivity of the electrically conductive sample liquid are temperature corrected measured magnitudes.

7. An apparatus, comprising:
a memory storing computer code; and
a data processor configured to execute the computer code to execute the method of claim 1.

8. An analyser, comprising:
a spectrometer;
an electrical property sensor; and
the apparatus of claim 7, wherein the data processor of the apparatus is configured to standardize an output of the electrical property sensor based at least in part upon spectra data obtained from the spectrometer.

9. A non-transitory computer readable medium storing a computer code that is executable by a data processor to cause the data processor to execute the method of claim 1.

* * * * *